(12) United States Patent
Greenberg

(10) Patent No.: US 7,989,418 B2
(45) Date of Patent: Aug. 2, 2011

(54) METHODS FOR THE USE OF BRANCHED CHAIN AMINO ACIDS

(75) Inventor: Norman Alan Greenberg, New Hope, MN (US)

(73) Assignee: Nestec S.A., Vevey (CH)

( * ) Notice: Subject to any disclaimer, the term of this patent is extended or adjusted under 35 U.S.C. 154(b) by 188 days.

(21) Appl. No.: 12/089,970

(22) PCT Filed: Oct. 26, 2006

(86) PCT No.: PCT/US2006/041615
§ 371 (c)(1),
(2), (4) Date: Jun. 30, 2008

(87) PCT Pub. No.: WO2007/053390
PCT Pub. Date: May 10, 2007

(65) Prior Publication Data
US 2009/0170786 A1 Jul. 2, 2009

Related U.S. Application Data

(60) Provisional application No. 60/731,450, filed on Oct. 28, 2005.

(51) Int. Cl.
*A23L 1/305* (2006.01)
*A61K 38/05* (2006.01)
(52) U.S. Cl. ........ 514/5.5; 424/439; 426/648; 514/15.4; 514/21.91
(58) Field of Classification Search .......... None
See application file for complete search history.

(56) References Cited

U.S. PATENT DOCUMENTS

| | | | |
|---|---|---|---|
| 5,034,377 A | | 7/1991 | Adibi et al. |
| 5,525,350 A | * | 6/1996 | Hansen et al. ............ 424/438 |
| 2002/0044957 A1 | * | 4/2002 | Fuchs et al. ............ 424/439 |
| 2003/0099689 A1 | * | 5/2003 | Dabrowski et al. .......... 424/442 |
| 2003/0198617 A1 | | 10/2003 | Green et al. |
| 2004/0224037 A1 | * | 11/2004 | Romero-Matos ............ 424/760 |
| 2007/0122451 A1 | * | 5/2007 | Yamamoto et al. ........... 424/439 |
| 2009/0105123 A1 | * | 4/2009 | Tisdale et al. ................ 514/4 |
| 2009/0143301 A1 | * | 6/2009 | Olson et al. ................ 514/12 |

FOREIGN PATENT DOCUMENTS

| | | |
|---|---|---|
| EP | A1941896 | 7/2008 |
| JP | 2-22232 A * | 1/1990 |
| JP | 4-21635 A * | 1/1992 |
| JP | 2003-24012 A * | 1/2003 |
| WO | WO 2004/078780 | 9/2004 |
| WO | WO 2005/012334 A1 * | 2/2005 |

OTHER PUBLICATIONS

Asao et al. Quantitative Structure-Activity Relationships of the Bitter Thresholds of Amino Acids, Peptides, and Their Derivatives. 1987, vol. 30, No. 10, pp. 1873-1879.*

Ichimura et al. Angiotensin I-Converting Enzyme Inhibitory Activity and Insulin Secretion Stimulative Activity of Fermented Fish Sauce. Journal of Bioscience and Bioengineering. 2003, vol. 96, No. 5, pp. 496-499.*

Sforza et al. Oligopeptides and free amino acids in Parma hams of known cathepsin B activity. Food Chemistry. 2001, vol. 75, pp. 267-273.*

Machine Translation of JP 2003-24012, published Jan. 2003.*

* cited by examiner

*Primary Examiner* — Jeffrey E Russel
(74) *Attorney, Agent, or Firm* — Gary M. Lobel

(57) ABSTRACT

The invention provides an orally-administrable nutritional product comprising a dipeptide including a branched chain amino acid (BCAA). In one embodiment, the nutritional product comprises a dipeptide selected from at least one of the following: alanyl-leucine, alanyl-isoleucine, alanyl-valine, glycyl-leucine, glycyl-isoleucine, and glycyl-valine.

9 Claims, No Drawings

METHODS FOR THE USE OF BRANCHED CHAIN AMINO ACIDS

CROSS REFERENCE TO RELATED APPLICATIONS

This application is a national stage filing of PCT/US2006/041615, filed Oct. 26, 2006, which claims priority to U.S. Provisional Appl. No. 60/731,450, filed Oct. 28, 2005.

BACKGROUND OF THE INVENTION

1. Technical Field

The invention relates generally to use of branched chain amino acids and more particularly to the use of dipeptides including branched chain amino acids to reduce bitterness in orally-administrable nutritional products.

2. Background Art

Amino acids are the monomeric building blocks of proteins, which in turn comprise a wide range of biological compounds, including enzymes, antibodies, hormones, transport molecules for ions and small molecules, collagen, and muscle tissues. Amino acids are considered hydrophobic or hydrophilic, based upon their solubility in water, and, more particularly, on the polarities of their side chains. Amino acids having polar side chains are hydrophilic, while amino acids having nonpolar side chains are hydrophobic. The solubilities of amino acids, in part, determines the structures of proteins. Hydrophilic amino acids tend to make up the surfaces of proteins while hydrophobic amino acids tend to make up the water-insoluble interior portions of proteins.

Of the common 20 amino acids, nine are considered essential in humans, as the body caimot synthesize them. Rather, these nine amino acids must be obtained through an individual's diet. A deficiency of one or more amino acids can cause a negative nitrogen balance, wherein more nitrogen is excreted than is ingested as proteins are degraded faster than they are synthesized. Such a condition can lead to disruption of enzymatic activity and the loss of muscle mass.

A number of muscle-wasting conditions have been identified, for which treatment with amino acid supplements has proved beneficial. For example, cachexia is a severe body wasting condition characterized by marked weight loss, anorexia, asthenia, and anaemia. Cachexia is a common feature of a number of illnesses, such as cancer, sepsis, chronic heart failure, rheumatoid arthritis, and acquired immune deficiency syndrome (AIDS). In addition, it has been found that certain tumors may induce cachexia through the production of a 24 kDa glycoprotein called proteolysis-inducing factor (PIF). PIF decreases protein synthesis, activates protein degradation, and stimulates the ATP-proteasome-dependent pathway. It has been hypothesized that the decreased protein synthesis associated with PIF is the result of PIF's ability to block the translation process of protein synthesis. Another factor, Angiotensin II (Ang II) has shown similar effects and may be involved in the muscle wasting observed in some cases of cachexia. Other muscle wasting diseases and disorders are known, including, for example, sarcopenia, an age-related loss of muscle mass.

Treatment of conditions such as cachexia and sarcopenia often includes nutritional supplementation, and, in particular, amino acid supplementation, in an attempt to increase protein synthesis and/or counteract protein degradation. Branched chain amino acids (BCAAs), which include valine, leucine, and isoleucine, are especially useful in such cases, as they have been shown to function not only as protein building blocks, but also as inducers of signal transduction pathways that modulate translation initiation.

The wasting conditions above are just a few of the conditions, disorders, and diseases for which amino acid supplementation has proved beneficial. Amino acid supplementation has also been used to treat diabetes, hypertension, high levels of serum cholesterol and triglycerides, Parkinson's disease, insomnia, drug and alcohol addiction, pain, insomnia, and hypoglycemia. Supplementation with BCAAs, in particular, has been used to treat liver disorders, including compromised liver function, including cirrhosis, gall bladder disorders, chorea and dyskinesia, and kidney disorders, including uremia. BCAA supplementation has also proved successful in the treatment of patients undergoing hemodialysis, resulting in improvements in overall health and mood.

Unfortunately, BCAAs exhibit a strongly bitter taste. Some patients reject oral nutritional supplements containing BCAAs because of their objectionable taste, despite the physiological benefits such supplements offer. Attempts to overcome such rejection have included the addition of masking agents to the supplement, which attempt to block the perception of bitterness, and the addition of other strong flavors, such as chocolate mint. Neither of these attempts has proved satisfactory. Masking agents generally do not completely block a patient's perception of bitterness and the addition of other strong flavors, while not bitter, are often equally objectionable to patients with limited appetites and/or nausea.

Accordingly, there is a need in the art for an orally-administrable nutritional product and method for its administration that do not suffer from the deficiencies above.

SUMMARY OF THE INVENTION

The invention provides an orally-administrable nutritional product comprising a dipeptide including a branched chain amino acid (BCAA). The nutritional products of the present invention may be used to maintain or promote a nitrogen balance in an individual suffering from a disease, disorder, stress, or a consequence of aging. The products of the present invention may similarly be used to maintain or promote a nitrogen balance in an otherwise healthy individual but who may be at risk for developing a nitrogen imbalance, such as an individual engaged in athletic performance or other physically strenuous activity. In one embodiment, the nutritional product comprises a dipeptide selected from at least one of the following: alanyl-leucine, alanyl-isoleucine, alanyl-valine, glycyl-leucine, glycyl-isoleucine, and glycyl-valine.

A first aspect of the invention provides an orally-administrable nutritional product comprising: at least one dipeptide including at least one branched chain amino acid, wherein the at least one dipeptide exhibits a bitterness less than that of a free branched chain amino acid.

A second aspect of the invention provides a method of treating an individual suffering from at least one of a disease and a disorder with an orally-administrable nutritional product, the method comprising: administering to the individual an orally-administrable nutritional product including: an effective amount of at least one dipeptide including at least one branched chain amino acid, wherein the dipeptide exhibits a bitterness less than that of a free branched chain amino acid.

The illustrative aspects of the present invention are designed to solve the problems herein described and other problems not discussed, which are discoverable by a skilled artisan.

DETAILED DESCRIPTION

As indicated above, the present invention relates to the use of a dipeptide including a branched chain amino acid (BCAA) to reduce bitterness in an orally-administrable nutritional product.

As used herein, the terms "treatment" and "treat" refer to both prophylactic or preventive treatment and curative or disease-modifying treatment, including treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as nitrogen imbalance, due to, for example, strenuous physical activity. Consequently, an "effective amount" is an amount that treats a disease or medical condition in an individual or, more generally, provides a nutritional, physiological, or medical benefit to the individual.

Surprisingly, it has been found that dipeptides of a branched chain amino acid (BCAA) and a second amino acid do not exhibit the bitterness of the free branched chain amino acid. A dipeptide is formed by the joining of the α-carboxyl group of one amino acid to the α-amino group of another amino acid. In one preferred dipeptide of the present invention, the second amino acid is alanine. In another preferred dipeptide of the present invention, the second amino acid is glycine. The preferred dipeptides according to the present invention, therefore, are alanyl-leucine, alanyl-isoleucine, alanyl-valine, glycyl-leucine, glycyl-isoleucine, and glycyl-valine. It should be recognized, however, that any amino acid may be used in the dipeptides of the present invention, including a second BCAA. The dipeptides of the present invention may be produced by any known or later-developed method, including synthetic production.

Equal molar concentrations of free leucine and the alanyl-leucine dipeptide were tasted after being dissolved in water and after being added to a standard vanilla oral nutritional supplement. In each instance, the alanyl-leucine dipeptide was found to exhibit less bitterness than free leucine. The tests were repeated, comparing free isoleucine to the alanyl-isoleucine dipeptide and free valine to the alanyl-valine dipeptide. Again, in each instance, the dipeptide was found to exhibit less bitterness than the free BCAA. The dissolved alanyl-leucine dipeptide was also compared to Novartis' RESOURCE® Support®, a nutritional product containing approximately 3.2 g of free leucine per 8 oz. serving. The dissolved alanyl-leucine dipeptide exhibited less bitterness than RESOURCE® Support®.

Accordingly, the present invention includes orally-administrable nutritional products that substitute, in whole or in part, a dipeptide including a BCAA for the free BCAA normally used. As noted above, preferred dipeptides include one of alanine and glycine and a BCAA, specifically alanyl-leucine, alanyl-isoleucine, alanyl-valine, glycyl-leucine, glycyl-isoleucine, and glycyl-valine dipeptides. The orally-administrable nutritional product of the present invention may further contain any number of ingredients that provide a nutritional, physiological, or medical benefit to an individual. Such ingredients include, for example, proteins, soluble and/or insoluble fibers, fatty acids, vitamins, minerals, sugars and/or other carbohydrates, flavor agents, and medicaments or other therapeutic agents. The present invention further includes methods for the administration of such orally-administrable nutritional products to an individual.

The products and methods of the present invention may be used, therefore, to treat an individual suffering from one or more of the following: cachexia, cancer, tumor-induced weight loss, sepsis, chronic heart failure, rheumatoid arthritis, acquired immune deficiency syndrome (AIDS), sarcopenia, diabetes, hypertension, high levels of serum cholesterol, high levels of triglycerides, Parkinson's disease, insomnia, drug addiction, alcohol addiction, pain, insomnia, hypoglycemia, compromised liver function, including cirrhosis, gall bladder disorders, chorea, dyskinesia, and a kidney disorder, including uremia. In addition, the products and method of the present invention may be used to treat an individual undergoing hemodialysis.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of treating an individual suffering from at least one of a disease and a disorder with an orally-administrable nutritional product, the method comprising:
   administering to the individual an orally-administrable nutritional product including:
   an effective amount of at least one dipeptide including at least one branched chain amino acid,
   wherein the dipeptide exhibits a bitterness less than that of a free branched chain amino acid, and wherein the individual is being treated using hemodialysis.

2. The method of claim 1, wherein the branched chain amino acid is selected from the group consisting of leucine, isoleucine, valine, and combinations thereof.

3. The method of claim 1, wherein the at least one dipeptide further includes one of alanine and glycine.

4. The method of claim 1, wherein the dipeptide is selected from a group consisting of alanyl-leucine, alanyl-isoleucine, alanyl-valine, glycyl-leucine, glycyl-isoleucine, glycyl-valine, and combinations thereof.

5. The method of claim 1, wherein the orally-administrable nutritional product further comprises at least one of a protein, a fiber, a fatty acid, a vitamin, a mineral, a carbohydrate, a flavor agent, a medicament, and a therapeutic agent.

6. The method of claim 1, wherein the orally-administrable nutritional product further comprises at least one fiber.

7. The method of claim 1, wherein the orally-administrable nutritional product further comprises at least one vitamin.

8. The method of claim 1, wherein the orally-administrable nutritional product further comprises at least one mineral.

9. The method of claim 1, wherein the orally-administrable nutritional product further comprises at least one flavor agent.

* * * * *